(12) United States Patent
Sailor et al.

(10) Patent No.: US 8,308,066 B2
(45) Date of Patent: Nov. 13, 2012

(54) METHOD FOR FORMING OPTICALLY ENCODED THIN FILMS AND PARTICLES WITH GREY SCALE SPECTRA

(75) Inventors: Michael J. Sailor, La Jolla, CA (US); Shawn O. Meade, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 1520 days.

(21) Appl. No.: 10/589,741

(22) PCT Filed: Dec. 21, 2004

(86) PCT No.: PCT/US2004/042997
§ 371 (c)(1),
(2), (4) Date: Aug. 16, 2006

(87) PCT Pub. No.: WO2005/062865
PCT Pub. Date: Jul. 14, 2005

(65) Prior Publication Data
US 2007/0051815 A1    Mar. 8, 2007

Related U.S. Application Data

(60) Provisional application No. 60/532,144, filed on Dec. 22, 2003.

(51) Int. Cl.
G06K 7/10 (2006.01)
G06K 7/14 (2006.01)

(52) U.S. Cl. ........................................ 235/454; 235/435

(58) Field of Classification Search .................. 235/435, 235/454
See application file for complete search history.

(56) References Cited

U.S. PATENT DOCUMENTS
4,390,452 A    6/1983 Stevens
(Continued)

FOREIGN PATENT DOCUMENTS
WO    WO 03/067231    8/2003
(Continued)

OTHER PUBLICATIONS

Eric J. Lee et al., "Photoderivation of the Surface of Luminescent Porous Silicon with Formic Acid", *J. Am. Chem. Soc.*, vol. 117, 8295-96 (1995).
(Continued)

*Primary Examiner* — Kristy A Haupt
(74) *Attorney, Agent, or Firm* — Greer, Burns & Crain Ltd.

(57) ABSTRACT

The invention concerns a method of making a thin film and/or particle having a grey scale code embedded in its physical structure by refractive index changes between different regions of the thin film or particle, as well as thin films and particles made by the method. In a preferred method for encoding a thin film, a semiconductor or insulator substrate is etched to form a thin film including pores. The etching conditions are controlled to vary porosity in the thin film according to a pattern that will generate an optical signature in the reflectivity spectrum in response to illumination such that the optical signature will including a grey scale code. The etching waveform is formed by the addition of at least two separate sine components in accordance with the following equations (1) $A_n=(A_{nmax}-A_{nmin})/2$; (2) $k_n$=frequency=1/period; (3) $y_n=A_n[\sin(k_n t-\Phi)+1]+A_{nmin}$ (4) $y_{comp}=[y_1+ \ldots +y_n]/n$ wherein equation (1) defines the amplitude of sine component n, which results in the spectral peak height, or grey scale of a bit; Equation (2) defines the frequency of the each sine component, which results in the spectral position of a peak, or identification of a bit (1st bit, 2nd bit, etc. . . );. Equation (3) defines sine component n and Equation (4) defines the composite waveform used to drive the electrochemical etch. The film can be removed and diced into particles.

24 Claims, 2 Drawing Sheets

U.S. PATENT DOCUMENTS

| | | | |
|---|---|---|---|
| RE33,581 | E | 4/1991 | Nicoli et al. |
| 5,071,248 | A | 12/1991 | Tiefenthaler et al. |
| 5,218,472 | A | 6/1993 | Jazefowicz et al. |
| 5,301,204 | A | 4/1994 | Cho et al. |
| 5,318,676 | A | 6/1994 | Sailor et al. |
| 5,468,606 | A | 11/1995 | Bogart et al. |
| 5,763,176 | A | 6/1998 | Slater et al. |
| 5,928,726 | A | 7/1999 | Butler et al. |
| 6,096,496 | A | 8/2000 | Frankel |
| 6,130,748 | A | 10/2000 | Kruger et al. |
| 6,206,065 | B1 | 3/2001 | Robbie et al. |
| 6,248,539 | B1 | 6/2001 | Ghadiri et al. |
| 6,255,709 | B1 | 7/2001 | Marso et al. |
| 6,355,431 | B1 | 3/2002 | Chee et al. |
| 6,396,995 | B1 | 5/2002 | Stuelpnagel et al. |
| 6,429,027 | B1 | 8/2002 | Chee et al. |
| 6,465,193 | B2 | 10/2002 | Akeson et al. |
| 6,544,732 | B1 | 4/2003 | Chee et al. |
| 6,620,584 | B1 | 9/2003 | Chee et al. |
| 6,663,832 | B2 | 12/2003 | Lebl et al. |
| 6,690,027 | B1 | 2/2004 | Bensahel et al. |
| 6,770,441 | B2 | 8/2004 | Dickinson et al. |
| 6,812,005 | B2 | 11/2004 | Fan et al. |
| 6,846,460 | B1 | 1/2005 | Lebl |
| 6,858,394 | B1 | 2/2005 | Chee et al. |
| 6,919,009 | B2 | 7/2005 | Stonas et al. |
| 7,225,082 | B1 | 5/2007 | Natan et al. |
| 7,241,629 | B2 | 7/2007 | Dejneka et al. |
| 2003/0129778 | A1 | 7/2003 | Bastian et al. |

FOREIGN PATENT DOCUMENTS

| | | | |
|---|---|---|---|
| WO | WO 03/067231 A | * | 8/2003 |

OTHER PUBLICATIONS

V.S.Y. Lin et al., "A Porous Silicon-Based Optical Interferometric Biosensor", *Science*, vol. 278, pp. 840-842 (Oct. 31, 1997).
Andreas Janshoff et al., "Macroporous p-Type Siicon Fabry-Perot Layers. Fabrication, Characterization, and Applicationsin Biosensing", *J. Am. Chem. Soc.*, vol. 120, pp. 12108-12116 (1998).
S. R. Nicewarner-Peña et al., "Submicrometer Metallic Barcodes", *Science*, vol. 294, pp. 137-141 (Oct. 5, 2001).
L. Pavesi et al., "Random Porous Silicon Multilayers: Application to Distributed Bragg Reflectors and Interferential Fabry-Pérot Filters", *Semicond. Sci. Technol.*, vol. 12, pp. 570-575 (1997).
D. Van Noort et al., "Monitoring Specific Interaction of Low Molecular Weight Biomolecules on Oxidized Porous Silicon Using Ellipsometry", *Biosensors & Bioelectronics*, vol. 13, No. 3-4, pp. 439-449 (1998).
M. Thonissen et al., Section 1.4, "Multilayer Structures of Porous Silicon", in *Properties of Porous Silicon*, (Eds: L. Canham). EMIS Datareviews, vol. 8, Short Run Press Ltd., London, pp. 30-37 (1997).
Honglae Sohn et al., "Detection of Fluorophosphonate Chemical Warefare Agents by Catalytic Hydrolysis with a Porous Silicon Interferometer", *J. Am. Chem. Soc.*, vol. 122, pp. 5399-5400 (2000).
M.J. Sailor, "Sensor Applications of Porous Silicon", Section 12.4, In *Properties of Porous Silicon*, (Eds: L. Canham). EMIS Datareviews, vol. 8, Short Run Press Ltd., London, pp. 364-370 (1997).
J.R. Quagliano et al., "Quantitative Chemical Identification of Four Gases in Remote Infrared (9-11 µm) Differential Absorption Lidar Experiments", *Applied Optics*, vol. 36, No. 9, pp. 1915-1927 (Mar. 20, 1997).
M.J. Sailor et al., "Low-Power Microsenors for Explosives and Nerve Warfare Agents Using Silicon Nanodots and Nanowires", in SPIE Meeting on Unattended Ground Sensor Technologies and Applications, (Ed: E.M. Carapezza, D.B. Law and K.T. Stalker). SPIE, 2000.
B. Warneke et al., "Smart Dust: Communicating with a Cubic-Millimeter Computer", *Computer*, pp. 44-51 (Jan. 2001).
V.G. Cheung et al., "Making and Reading Microarrays", *Nature Genetics Supplement*, vol. 21, pp. 15-19, (Jan. 1999).
L.T. Canham et al., "Derivatized Porous Silicon Mirrors: Implantable Optical Components with Slow Resorbability", *Physica*, vol. 182, No. 1, pp. 521-525 (2000).

A.P. Bowditch, "In-Vivo Assessment of Tissue Compatibility and Calcification of Bulk and Porous Silicon", *Materials Research Society Symp. Proc.*, vol. 536, pp. 149-154 (1999).
S. Chan et al., "Porous Silicon Microcavities for Biosensing Applications", *Phys. Stat. Sol.*, vol. 182, pp. 541-546 (2000).
"Abstracts of Oak Ridge Posters", *Clinical Chem.*, vol. 46, No. 9, pp. 1487-1522 (2000).
K.P.S. Dancil et al., "A Porous Silicon Optical Biosensor: Detection of Reversible Binding of IgG to a Protein A-Modified Surface," *J. Am. Chem. Soc.*, vol. 121, pp. 7925-7930 (1999).
J.H. Holtz et al., "Polymerized Colloidal Crystal Hydrogel Films as Intelligent Chemical Sensing Materials", *Nature*, vol. 389, pp. 829-832 (Oct. 23, 1997).
J. Gao et al., "Porous-Silicon Vapor Sensor Based on Laser Interferometry": *Applied Physics Letters*, vol. 77, No. 6, pp. 901-903 (Aug. 7, 2000).
J.M. Lauerhaas et al., "Chemical Modification of the Photoluminescence Quenching of Porous Silicon", *Science*, vol. 261, pp. 1567-1568 (Sep. 17, 1993).
J.L. Heinrich et al., "Luminescent Colloidal Silicon Suspensiosn from Pourous Silicon", *Science*, vol. 255, No. 5040, pp. 66-68 (Jan. 3, 1992).
M.D. Ray et al., "Ultraviolet Mini-Raman Lidar for Stand-Off, in situ, Identification of Chemical Surface Contaminants", *Review of Scientific Instruments*, vol. 71, No. 9, pp. 3485-3489 (Sep. 2000).
N.F. Starodub et al., "Use of the Silicon Crystals Photoluminescence to Control Immunocomplex Formation", *Sensors and Actuators*, pp. 44-47, (1996).
M.J. Sailor et al., "Detection of DNT, TNT, HF and Nerve Agents Using Photoluminescence and Interferometry from a Porous Silicon Chip", *In Unattended Ground Senor Technologies and Applications II*, Proceedings of SPIE, vol. 4040, pp. 95-104 (2000).
L. Pavesi et al., "Controlled Photon Emission in Porous Silicon Microcavities", *Appl. Phys. Lett.*, vol. 67, No. 22, pp. 3280-3282 (Nov. 27, 1995).
C. Mazzoleni et al., "Application to Optical Components of Dielectric Porous Silicon Multilayers", *Appl. Phys. Lett.*, vol. 67, No. 20, pp. 2983-2985 (Nov. 13, 1995).
V. Lehmann et al., "Optical Shortpass Filters Based on Macroporous Silicon", *Applied Physics Letters*, vol. 78, No. 5, pp. 589-591 (Jan. 29, 2001).
A.M. Tinsley-Bown et al., "Tuning the Pore Size and Surface Chemistry of Porous Silicon for Immunoassays", *Phys. Stat. Sol.*, vol. 182, pp. 547-553 (2000).
P.A. Snow et al., "Vapor Sensing using the Optical Properties of Porous Silicon Bragg Mirrors", *Journal of Applied Physics*, vol. 86, No. 4, pp. 1781-1784 (Aug. 15, 1999).
G. Vincent, "Optical Properties of Porous Silicon Superlattices", *Appl. Phys. Lett.*, vol. 64, No. 18, pp. 2367-2369 (May 2, 1994).
V. Wulmeyer et al., "Ground-Based Differential Absorption Lidar for Water-Vapor Profiling: Assessment of Accuracy, Resolution, and Meteorological Applications", *Applied Optics*, vol. 37, No. 18, pp. 3825-3844 (Jun. 20, 1998).
M. Bruchez, Jr. et al., "Semiconductor Nanocrystals as Fluorescent Biological Labels", *Science*, vol. 281, pp. 2013-2016 (Sep. 25, 1998).
C.B. Carlisle et al., "$CO_2$ Laser-Based Differential Absorption Lidar System for Range-Resolved and Long-Range Detection of Chemical Vapor Plumes", *Applied Optics*, vol. 34, No. 27, pp. 6187-6200 (Sep. 20, 1995).
S. Chan et al., "Identification of Gram Negative Bacteria Using Nanoscale Silicon Microcavities", *J. Am. Chem. Soc.*, vol. 123, No. 47, pp. 11797-11798 (2001).
C.L. Curtis et al., "Observation of Optical Cavity Modes in Photoluminescent Porous Silicon Films", *J. Electrochem. Soc.*, vol. 140, No. 12, pp. 3492-3494 (Dec. 1993).
S. Content et al., "Detection of Nitrobenzene, DNT, and TNT Vapors by Quenching of Porous Silicon Photoluminescence", *Chem. Eur. J.*, vol. 6, No. 12, pp. 2205-2213 (2000).
D. Gerion et al., "Synthesis and Properties and Biocompatible Water-Soluble Silica-Coated CdSe/ZnS Semiconductor Quantum Dots", *J. Phys. Chem. B*, vol. 105, pp. 8861-8871 (2001).

M.R. Henry, et al., "Real-Time Measurements of DNA Hybridization on Microparticles with Fluorescence Resonance Energy Transfer", *Analytical Biochemistry*, vol. 276, pp. 204-214 (1999).

P. Coronado et al., "New Technologies to Support Nasa's Mission to Planet Earth Satellite Remote Sensing Product Validation: The Use of an Unmanned Autopilotd Vehicle (UAV) as a Platform to Conduct Remote Sensing", Part of the SPIE Conference on Robotic and Semi-Robotic Ground Vehicle Technology, Orlando, FL Apr. 1998, vol. 3366, pp. 38-49.

D.F. Shriver, "The Manipulation of Air-Sensitive Compounds", 2d Ed., John Wiley & Sons, Inc. New York, 1986, pp. 290-311.

F. Cunin et al., "Biomolecular Screening with Encoded Porous-Silicon Photonic Crystals", Nature Materials, vol. 1, pp. 39-41. (Sep. 2002).

M.G. Berger et al., "Dielectric Filter Made of Porous Silicon: Advanced Performance by Oxidation and New Layer Structures", Thin Solid Films, vol. 297, pp. 237-240 (1997).

H.. Fenniri et al., J. Am. Chem. Soc., vol. 123, pp. 8151-8152 (2001).

H. Fenniri et al., Angew. Chem. Int. Ed., vol. 39, pp. 4483-4485 (2000).

W.C.W. Chan et al., "Quantum Dot Bioconjugates for Ultrasensitive Nonisotopic Detection", Science, vol. 281, pp. 2016-2018 (1998).

J.A. Ferguson et al., "A Fiber Optic DNA Biosensor Microarray for the Analysis of Gene Expression", Nature Biotechnol, vol. 14, pp. 1681-1684 (1996).

M. Thonissen et al., Properties of Porous Silicon, vol. 18, pp. 12-22, (ed. L. Canham) (Short Run, London 1997).

A. Halimaoui, Properties of Porous Silicon, vol. 18, pp. 12-22, (ed. L. Canham) (Short Run, London 1997).

Vuckovic et al., "Optimization of Three-Dimensional Micropost Microcavities for Cavity Quantum Electrodynamics", Physical Review A., vol. 66, 2002, pp. 023808-1-023808-9.

Fauchet, Philippe M., "The integration of nanoscale porus silicon light emitters: materials, science, properties, and integration with electronic circuitry" *Journal of Luminescence*, 80, 1990, pp. 53-64.

Janshoff, Andreas et. al., "Macroporous p-Type Fabry-Perot Layers, Fabrication, Characterization and Applications in Biosensing", *Journal of American Chemical Society*, 1998, 120, pp. 12108-12116.

Lammel, G. et al., "Microspectrometer based on a tunable optical filter of porous silicon", *Sensors and Actuators*, A 92, 2001, pp. 52-59.

Letant, Sonia E. et. al., "Molecular identification by Time-Resolved Interfermetry in a Porous Silicon Film", *Advanced Materials*, 2001, 13, pp. 335-338.

Mattei, G., et. al., "Enhancement of adsorbate vibrations due to interaction with microcavity mode in porous silicon superlattice", *Surface Science*, 427-428 (1999) 235-238.

Setzu, S. et. al, "Optical properties of multilayered porous silicon", *Materials Science and Engineering*, B69-70, 2000, pp. 34-42.

Squire, E.K. et. al., "Light emission from porous silicon single and multiple cavities", *Journal of Luminescence*, 80, 1999, pp. 125-128.

Zhou, V. et. al., "The Effect of Thermal Processing on Mulitlayer Porous Silicon Microcavity", *Phsy. Stat. Sol.*, 182, 2000, pp. 319-324.

Office Action from U.S. Appl. No. 10/503,217, filed Feb. 5, 2010, Sailor et. al.

* cited by examiner

METHOD FOR FORMING OPTICALLY ENCODED THIN FILMS AND PARTICLES WITH GREY SCALE SPECTRA

PRIORITY CLAIM

Applicant claims priority benefits under 35 U.S.C. § 119 on the basis of Patent Application No. 60/532,144, filed Dec. 22, 2003.

STATEMENT OF GOVERNMENT INTEREST

This invention was made with Government assistance under DARPA Grant No. DASG60-03-C-0014. The Government has certain rights in this invention.

TECHNICAL FIELD

A field of the invention is encoding. Additional exemplary fields of the invention include the life sciences, security, product marking, food processing, agriculture, and chemical detection.

BACKGROUND ART

A well-appreciated need for labeling exists in society. Labeling is a fundamental basis for tracking and identifying. Encoding can be used as a form of labeling understood by persons or equipment, as in the case of bar coding. At the microscale, however, labeling/encoding itself becomes difficult.

Strategies to encode microscale materials have accordingly received increased attention for such uses as high-throughput screening in the fields of drug discovery, genetics screening, biomedical research, and biological and chemical sensing. Concurrent research strategies for measuring an increased number of analytes while minimizing the necessary sample volume have focused on either on-chip spatially differentiated arrays or encoded beads. Large arrays have been developed for biological and/or chemical sensing purposes by making use of positional encoding to register specific analyte responses. The main advantage of using an array over a conventional single analyte sensor is the ability to process and analyze a large number of analytes simultaneously. Positional arrays, however, can suffer from slow diffusion rates and limits on the concentration ranges of analytes being sensed. An alternative approach is to use individually encoded beads.

Early attempts to encode particles used fluorescent or infrared-active molecules as binary markers. More recently, cadmium selenide quantum dots have been demonstrated as viable candidates for particle encoding based on their unique fluorescent properties. Quantum dots have the advantage over organic molecules of increased stability towards photobleaching, sharper fluorescence peaks, improved solubility characteristics, and large excitation frequency ranges. With six colors (limited to the peak width of the fluorescence in the visible range) and ten intensity levels, $10^6$ particles could theoretically be encoded. In practice, this number is difficult to obtain because of spectral overlap and sample inhomogeneities. Also, despite the increased photostability of quantum dots, fluorescence quenching is still possible, casting uncertainty on using relative intensity measurements as a reliable encoding method.

Another encoding strategy has used sub-micron metallic rods. The sub-micron metallic rods are prepared by electrodeposition of metals on a porous membrane in alternating strips of controlled thickness. Different reflection characteristics of the various metals are used as a barcode for identification purposes. Reflection spectroscopy does not have the disadvantage of photobleaching inherent with fluorophores. Additionally, fluorescent analytes do not interfere with the particle signal. Deposition of rods is a relatively complex process, however, and may be difficult to apply as an encoding strategy where, for example, a large number of codes is desirable because each rod must be brought into focus in an optical reader (such as a microscope) in order to read out the codes. There remains a need for encoding strategies at the microscale.

DISCLOSURE OF THE INVENTION

The invention concerns a method of making a thin film and/or particle having a grey scale code embedded in its physical structure by refractive index changes between different regions of the thin film or particle, as well as thin films and particles made by the method. In a preferred method for encoding a thin film, a semiconductor or insulator substrate is etched to form a thin film including pores. The etching conditions are controlled to vary porosity in the thin film according to a pattern that will generate an optical signature in the reflectivity spectrum in response to illumination such that the optical signature will including a grey scale code. The etching waveform is formed by the addition of at least two separate sine components in accordance with the following equations (1) $A_n = (A_{nmax} - A_{nmin})/2$; (2) $k_n = \text{frequency} = 1/\text{period}$; (3) $y_n = A_n[\sin(k_n t - \Phi) + 1] + A_{nmin}$ (4) $y_{comp} = [y_1 + \ldots + y_n]/n$ wherein equation (1) defines the amplitude of sine component n, which results in the spectral peak height, or grey scale of a bit; Equation (2) defines the frequency of the each sine component, which results in the spectral position of a peak, or identification of a bit (1st bit, 2nd bit, etc. . . .); Equation (3) defines sine component n and Equation (4) defines the composite waveform used to drive the electrochemical etch. The film can he removed and diced into particles.

BEST MODE OF CARRYING OUT THE INVENTION

The invention concerns a particle having a grey scale code embedded in its physical structure by refractive index changes between different regions of the particle. A change in the refractive index is preferably obtained by varying porosity formed in the particle. Reflections taken from the particles produce an optical signature, in the visible and/or non-visible wavelengths. In preferred embodiments, the number of peaks, their locations, and intensities can be used to produce a high number of unique optical signatures exhibiting grey scale codes. In preferred embodiment formation methods, a porous encoded structure is produced by an etching process during which the etching conditions are varied during pore formation according to a computer generated waveform designed to produce a grey scale coding. A dicing may be conducted to form individual encoded particles having a range of small sizes, e.g., from hundreds of nanometers to hundreds of microns.

Methods and particles of the invention are applicable to a variety of industries, including but not limited to drug discovery, biological screening, chemical screening, biological labeling, chemical labeling, in vivo labeling, security identification and product marking. Various attributes of the particles and methods of the invention enable a wide range of applications in various industries. The small size of the particles facilitates ready incorporation into various hosts, e.g., products, test kits, assays, powders (such as explosives for identification), pastes, liquids, glass, paper, and any other host or system that can accept small particles. In vivo detection is enabled by biocompatible particles of the invention, which may then be queried, for example, through tissues using near infrared and infrared wavelengths that penetrate tissues.

In accordance with the aforementioned exemplary aspects and applications of the inventions, preferred embodiment particles are identified by the grey scale code inherent to the reflectivity spectrum of their varying porous structure. In another aspect of the invention, matter, e.g., biological or chemical matter, is hosted by the porous structure and the particle becomes a tag identifying the matter hosted by the pores. In another aspect of the invention, a variance in the reflectivity spectrum of an encoded particle can indicate the presence, absence or quantity of matter within the particle's pores.

Figure 1:
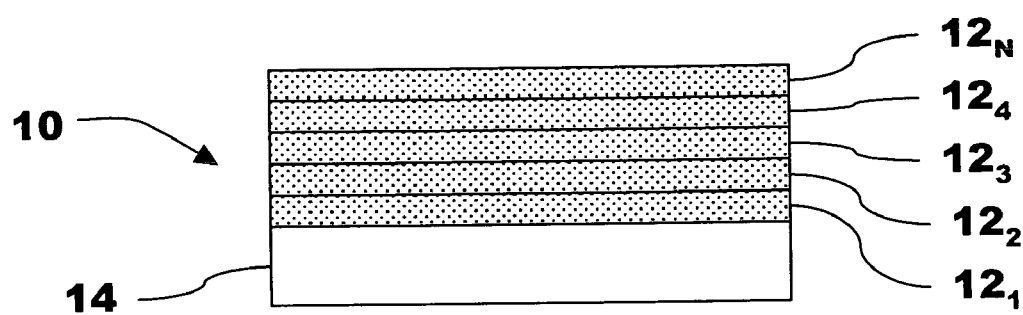
FIG. 1 is a schematic diagram of a multi-layer encoded particle of the invention.

Referring to FIG. 1, a preferred embodiment encoded particle 10 is shown in cross-section. The encoded particle 10 includes a porous thin film 12. The porous thin film 12 having varying porosity is shown in FIG. 1 as being formed on a substrate 14. However, embodiments of the invention include particle structures released from a substrate upon or from which they were initially formed. The thin film 12 is encoded to produce an interference pattern in the reflectivity spectrum that forms an optical signature including a grey scale code. Particles 10 of the invention may be specifically encoded by controlling etching conditions according to a computer generated waveform during formation of the particle 10.

The porous thin film 12 may be formed of any porous semiconductor or insulator. In preferred embodiment particles of the invention, porous silicon is used to form the thin film 12 Controlled anodic etching of crystal silicon in hydrofluoric acid solution permits control of both the porosity and thickness of porous thin film 12 The time of etching controls the thickness of a porous layer, while the etching current density controls the porosity. The thicknesses and porosities of thin films 12 are controlled in accordance with a computer generated waveform.

Porous silicon is a preferred material for the thin film 12. Porous silicon has a number of demonstrated advantages. For example, porous silicon has been demonstrated to be biocompatible. In addition, the surface chemistry of oxidized porous silicon is effectively that of silica. Accordingly, the surface chemistry is well understood for biochemical derivatization and ligand immobilization.

In preferred embodiments, the thin film 12 is formed to include a receptor material within the porous structure. The purpose of the receptor is to bind a particular analyte of interest. Exemplary receptors (also referred to as binders) are disclosed, for example, in U.S. Pat. No. 6,248,539 entitled "Porous Semiconductor Based Optical Interferometric Sensor". Receptor molecules may be adsorbed or otherwise associated with the porous silicon thin film 12 by any approach that leads to the tethering of the receptor molecules to the porous thin film 12. This includes, without limitation, covalently bonding the receptor molecules to the semiconductor, ionically associating the receptor molecules to the layers, adsorbing the receptor molecules onto the surface of the layers, or other similar techniques. Association can also include covalently attaching the receptor molecules to another moiety, which is in turn covalently bonded to the porous thin film 12, or binding the target molecule via hybridization or another biological association mechanism to another moiety which is coupled to the porous thin film 12. Specific additional examples include receptor ligands that have been attached to porous silicon layers to produce biosensors. An analyte bound to a particle 10 of the invention becomes identifiable and traceable by the encoding provided by the particle 10.

We have demonstrated reproducibility in the spectral position and grey level (spectral height) by using waveform and spectra design in accordance with equations 1-4:

$$A_n = (A_{nmax} - A_{nmin})/2 \quad (1)$$

$$k_n = \text{frequency} = 1/\text{period} \quad (2)$$

$$y_n = A_n[\sin(k_n t - \Phi) + 1] + A_{min} \quad (3)$$

$$y_{comp} = [y_1 30 \ldots + y_n]/n \quad (4)$$

Equation (1) defines the amplitude of sine component n, which results in the spectral peak height, or grey scale of a bit. Equation (2) defines the frequency of the each sine component, which results in the spectral position of a peak, or indentification of a bit (1st bit, 2nd bit, etc. . . . ). Equation (3) defines sine component n. Equation (4) defines the composite waveform used to drive the electrochemical etch. The spectral peak position is a function of the frequency, k, of the sine component y(t) of the time domain. Spectral peak position and position in k-space are synomomous and related by c=wavelength*k(frequency). Grey levels in the heights of the spectral lines can be determined based on each sine components' amplitude. Fourier analysis may be used as a modeling tool to approximate the spectra of the resulting photonic crystal in advance of the etching conducted to create the porosity pattern. The formation of a composite waveform may be achieved by the addition of two separate sine components in accordance with equation (4). In a porous silicon photonic crystal, the average amplitude of a composite waveform must stay the same if the spectral line group is to maintain the same absolute spectral position after a change in one or more of the sine components' amplitude. Consider, for example, two waveforms, wf_1 and wf_2, correspond to two codes of the form: Acomp (bit 1)=(A1+ . . . +An)/n; Acomp (bits 2 . . . n)={[A1−(x/(n−1))]+ . . . +[An+x]}/n. If the second code has amount x added to the amplitude of its sine component, then the following condition must be met: Acomp(wf−1)=Acomp(wf_2), where Acomp is the amplitude of the composite waveform formed from the addition of wf_1 and wf_2. Resultant k-space spectra will reveal that a constant position is maintained while amplitudes of sine components are changed with the above equations. When incident white light strikes the encoded film, only light containing frequencies that match the spatial frequencies of varying porosity present in the film are reflected back. This is a natural optical transform which is much like a Fourier transform.

Experiments were conducted to demonstrate the invention. Grey scale samples were prepared by anodically etching p++ type, B-dope, (100) oriented silicon with <1 mOhm-cm resistivity in a solution of 3:1 HF (48%, aq)/ethanol by volume. Computer generated anodic current waveforms consistent with the above explanations for grey scale coding were applied and a platinum mesh electrode was used as the counter electrode. Results were consistent with expectations.

The intensity of peaks in the reflectance spectrum is controlled by the refractive index at interfaces between thin film 12 determined by a change in porosity between adjacent layers. Such change may be gradual or sharp. The position of peaks is controlled by adjusting layer thicknesses. Additional encoding is possible by variation of the relative intensities of each reflectivity peak, which can be engineered into particles 10 of the invention by adjustment of the electro chemical etch parameters to control porosity of the thin film 12. A particle 10 having of the invention encodes $L^N$ codes, where N is the number of spectral lines and L is the number of grey levels possible in each spectral line.

Figure 2:
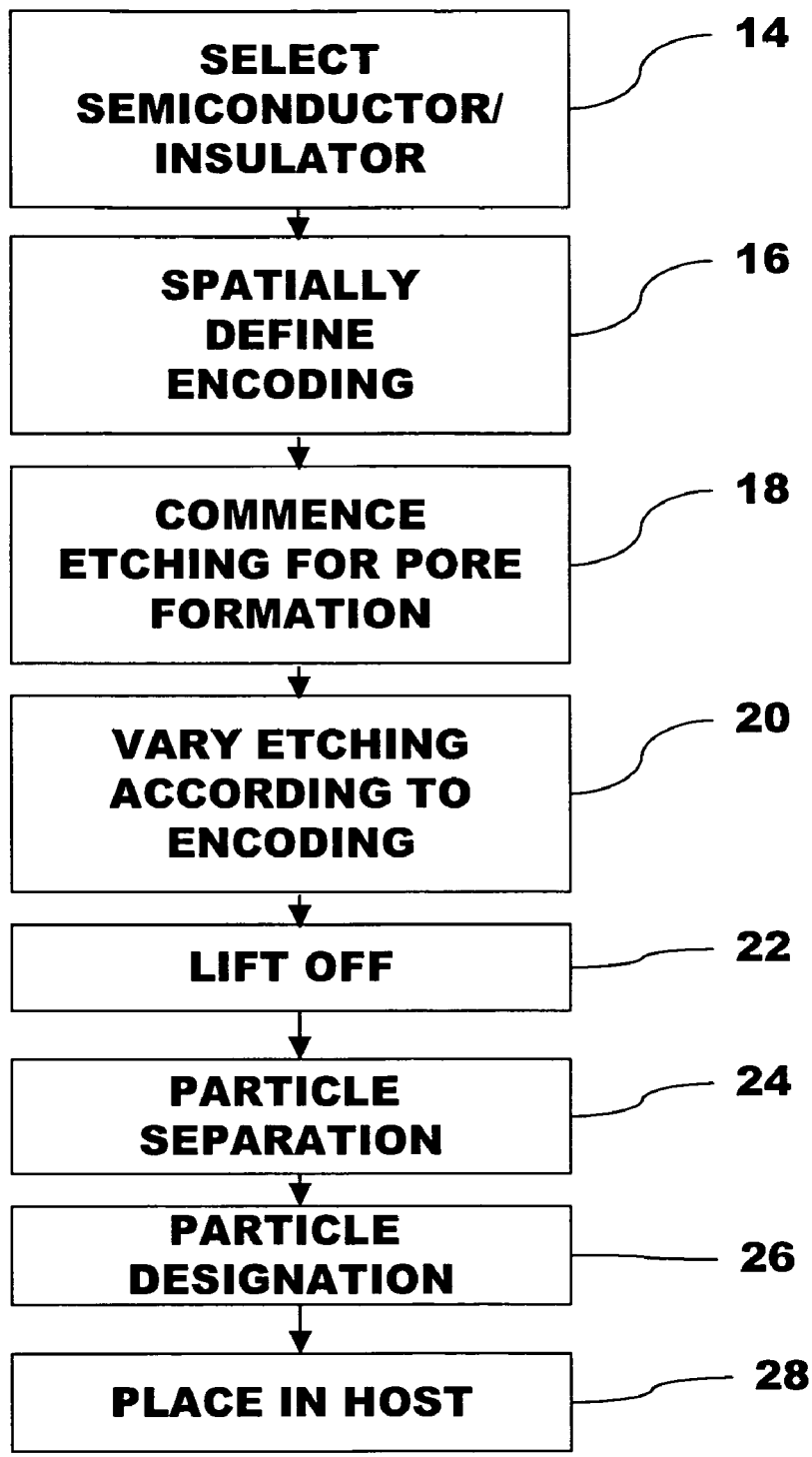
FIG. 2 illustrates a preferred embodiment method of fabricating encoded particles.

Referring now to FIG. 2, a preferred method for forming an encoded porous particle 10 is shown. A suitable semiconductor or insulator, e.g., a silicon wafer, is selected for processing (step 14). For example, silicon wafers may be cut to size and be masked to have portions exposed for etching. An exemplary suitable silicon material is a single crystalline silicon wafer. Spatial encoding is then defined (step 16). The spatial encoding defines a range of codes over the material to be etched. Conducting a spatially resolved etch allows codes to be programmed in particle-sized sections of the wafer. An exemplary spatially resolved etch is disclosed in U.S. Pat. No. 5,318,676, entitled "Photolithographic fabrication of luminescent images on porous silicon structures", published Jun. 7, 1994. In an alternative process, the step of spatial defining (step 16) is omitted. For example, a single wafer or an area of wafer could be etched to include particles having a single code. In that case, other wafers could be etched to have particles having a different code. Anodic etching is then commenced, for example, in an aqueous solution of hydrofluoric acid and ethanol (step 18). Etching is then conducted with etching conditions varying according to the defined encoding strategy (step 20). A grey scale code or codes of the invention are etched into the wafer. The traverse (vertical direction in FIG. 1) encoded but still connected particles may be lifted off from the silicon wafer (step 22), for example by a high level of electropolishing current. Areas between spatially defined etch sections may be cut to separate differently encoded wafer sections. Individual particles are then separated (step 24) in a dicing that may be conducted, for example, by mechanical agitation or ultrasonic fracturing. The particle separation (step 24) preferably produces micron-sized particles, e.g., particles in a range from a few hundred nanometers to a few hundred micrometers. A step of particle designation (step 26) may be conducted after the particle separation (step 24) or subsequent to step 20 or step 22. Particle designation may comprise, for example, chemical modification of the porous multi-layer structure $12_1$-$12_N$ for specific biological, biomedical, electronic, or environmental applications. As an example, the particles can be modified with a receptor for a desired analyte or with a targeting moiety (such as a sugar or a polypeptide). Additionally, binding can be signaled, for example, by fluorescence labeling of analytes or analyte autofluoresence. In use of particle 10, the particle can be identified by its optical signature upon binding of the designated targeted analyte. This step of designation may also be omitted in embodiments of the invention.

In other embodiments of the invention, encoded particles can be placed into a suitable hosts, namely any liquid, powder, dust, or other material that will hold encoded micron sized particles of the invention. Particles placed in hosts, for example, could be used to identify the source of a manufactured powder such as an explosive. Another potential host is an animal. Particles of the invention being biocompatible may be implanted in vivo into an animal host. The reflectivity spectrum of preferred embodiment porous silicon particles 10 of the invention, for example, encompasses the visible, near infrared, and infrared spectra. This presents the opportunity to sense the grey scale code of a particle of the invention through barriers such as living tissue.

A first example embodiment is stand-off detection. This is a chemical detection technique to identify an analyte from a distance. A particle 10 of the invention includes a receptor to sense a particular analyte. Both the grey scale code of the particle and an indication of binding of the analyte can be detected in the reflectivity spectrum, for example, with use of a low power laser. The receptor, for example, can be specific to sense biomolecules or to attach the encoded particle to a cell, spore, or pollen particle.

Another preferred exemplary application of the invention is for biomolecular screening via the encoded particle 10 of the invention. Millions of grey scale codes are possible with a small number of layers. A simple antibody-based bioassay using fluorescently tagged proteins has been tested. Periodic Rugate style encoding was used as described above with respect to the exemplary chemical sensing embodiments. By masking the wafer before etching, well-defined slabs of particles may be generated.

The layered grey scale porous-silicon encoded structures offer several advantages over existing encoding methodologies. Porous-silicon encoded structures can be constructed that display features spanning the visible, near-infrared and infrared regions of the spectrum. Unlike encoding schemes based on stratified metallic nanorods, fluorescence or vibrational signatures, encoded particles of the invention can be probed using light diffraction techniques; thus it is not necessary to use imaging optics in order to read the codes. Encoded particles may be assayed using a conventional fluorescence tagging technique, and sensitive chemical and biochemical detection can also be built into the optical structure of the encoded particles, eliminating the need for fluorescent probes and focusing optics. In addition, because preferred embodiment oxidized porous-silicon encoded particles present a silica-like surface to the environment, they do not readily quench luminescence from organic chromophores, and they can be handled and modified using the chemistries developed for glass bead bioassays. Silicon-based encoded particles may be readily integrated with existing chip technologies.

The use of encoded silicon particles of the invention in medical diagnostic applications has advantages over organic dyes or quantum dots. In vivo studies have shown the biocompatibility of porous silicon, as well as the long-term stability of reflectance data from multilayer structures. Additionally, the possibility of optically addressing particles at near-infrared, tissue-penetrating wavelengths without the losses associated with low fluorescence quantum yields makes these materials amenable to in vivo diagnostics. Finally, because the porous codes are an integral and orderly part of the porous structure, it is not possible for part of the code to be lost, scrambled or photobleached, as can occur with quantum dots or fluorescent molecules.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A method for encoding a thin film, comprising steps of:
   etching a semiconductor or insulator substrate to form a thin film including pores;
   varying etching conditions to vary porosity in the thin film according to a pattern that will generate an optical signature in the reflectivity spectrum in response to illumination, the optical signature including a grey scale code; wherein
   said step of varying comprises applying an etching waveform formed by the addition of at least two separate sine components in accordance with the following equations:

$$A_n = (A_{nmax} - A_{nmin})/2 \quad (1)$$

$$k_n = \text{frequency} = 1/\text{period} \quad (2)$$

$$y_n = A_n[\sin(k_n t - \Phi) + 1] + A_{nmin} \quad (3)$$

$$y_{comp} = [y_1 + \ldots + y_n]/n \quad (4)$$

wherein Equation (1) defines the amplitude of sine component n, which results in the spectral peak height, or grey scale of a bit; Equation (2) defines the frequency of the each sine component, which results in the spectral position of a peak, or identification of a bit (1st bit, 2nd bit, etc. . . );. Equation (3) defines sine component n, and Equation (4) defines the composite waveform used to drive the electrochemical etch.

2. The method of claim 1, wherein the grey scale code is revealed in naturally optically converted k-space.

3. The method according to claim 1, further comprising a step of separating the thin film from the semiconductor or insulator substrate.

4. The method according to claim 3, further comprising a step of separating the thin film into particles.

5. The method according to claim 4, further comprising a step of placing a particle within a host.

6. The method according to claim 4, further comprising steps of:
   generating an interference pattern in the reflectivity spectrum by illumination of one or more of the particles;
   determining a particle's code from the position and heights of peaks in k-space.

7. An encoded micron-sized particle having a grey scale code embedded in its physical structure by refractive index changes between different regions of the particle, the particle having been made by the method of claim 4.

8. The particle of claim 7, further comprising a receptor.

9. The particle of claim 8, wherein said receptor is a receptor for a biological analyte.

10. The particle of claim 8, wherein said receptor is a receptor for a chemical analyte.

11. The particle of claim 8, wherein said receptor is a receptor for a gaseous analyte.

12. The particle of claim 8, further comprising a fluorescence tag for assaying the particle.

13. The method according to claim 1, further comprising a step of spatially defining the semiconductor or insulator substrate to conduct said step of etching in a spatially defined location or locations.

14. The method according to claim 13, wherein said step of varying further varies etching conditions in different spatially defined locations to encode multiple codes in the thin film.

15. The method according to claim 14, further comprising a step of separating the thin film from the semiconductor or insulator substrate.

16. The method according to claim 15, further comprising a step of separating the thin film into particles.

17. A method for identification of an analyte bound to an encoded particle or identification of a host including an encoded particle of claim 4, the method comprising steps of:
   associating the one or more of the particles with the analyte or the host;
   generating an interference pattern in the reflectivity spectrum by illumination of the particle;
   determining the particle's code from the interference pattern;
   identifying the analyte or the host based upon said step of determining.

18. The method according to claim 17, further comprising a step of designating the particle to bind an analyte by modifying the particle with a specific receptor or targeting moiety.

19. The method according to claim 18, wherein the targeting moiety is a sugar or polypeptide.

20. The method according to claim 19, further comprising a step of signaling binding of an analyte by fluorescence labeling or analyte autofluorescence.

21. The method of claim 1, further comprising steps of:
   applying an electropolishing current to the wafer to remove the porous film from the wafer;
   dicing the film into micron-sized particles, each micron-sized particle maintaining an optical signature produced by said step of etching.

22. The method according to claim 21, further comprising a step of modifying the particles with a specific receptor or targeting moiety.

23. An encoded micron-sized thin film having a grey scale code embedded in its physical structure by refractive index changes between different regions of the thin film, the thin film having been made by the method of claim 1.

24. A method for encoding a thin film, comprising steps of:
   etching a semiconductor or insulator substrate to form a thin film including pores;
   adding multiple sine waveforms together in a computer memory to form a composite waveform that will be used to control etching of the semiconductor or insulator substrate, wherein the composite waveform has a pattern that will generate an optical signature in the reflectivity spectrum in response to illumination, the optical signature including a grey scale code;
   varying etching conditions according to the composite waveform.

* * * * *

UNITED STATES PATENT AND TRADEMARK OFFICE
CERTIFICATE OF CORRECTION

PATENT NO. : 8,308,066 B2
APPLICATION NO. : 10/589741
DATED : November 13, 2012
INVENTOR(S) : Michael J. Sailor et al.

Page 1 of 1

It is certified that error appears in the above-identified patent and that said Letters Patent is hereby corrected as shown below:

In the Specification:

Col. 2, line 37  Before "removed", please delete "he" and insert --be-- therefor.

Col. 4, line 20, Equation (4)

Please delete

"$y_{comp} = [y_1^{30} \ldots + y_n]/n$"

and insert

--$y_{comp} = [y_1 + \ldots + y_n]/n$-- therefor.

Signed and Sealed this
Fourteenth Day of May, 2013

Teresa Stanek Rea
*Acting Director of the United States Patent and Trademark Office*